US009532771B2

(12) United States Patent
Ferzli

(10) Patent No.: US 9,532,771 B2
(45) Date of Patent: Jan. 3, 2017

(54) SUPPORT COUPLING FOR SURGICAL INSTRUMENT

(71) Applicant: George S. Ferzli, Staten Island, NY (US)

(72) Inventor: George S. Ferzli, Staten Island, NY (US)

( * ) Notice: Subject to any disclaimer, the term of this patent is extended or adjusted under 35 U.S.C. 154(b) by 109 days.

(21) Appl. No.: 14/300,287

(22) Filed: Jun. 10, 2014

(65) Prior Publication Data

US 2014/0378996 A1 Dec. 25, 2014

Related U.S. Application Data

(63) Continuation-in-part of application No. 13/742,358, filed on Jan. 16, 2012, now abandoned.

(60) Provisional application No. 61/665,319, filed on Jun. 28, 2012.

(51) Int. Cl.
*A61B 17/00* (2006.01)
*A61B 1/00* (2006.01)

(52) U.S. Cl.
CPC ..... *A61B 17/00234* (2013.01); *A61B 1/00147* (2013.01); *A61B 90/11* (2016.02); *A61B 1/00131* (2013.01); *A61B 2017/00336* (2013.01)

(58) Field of Classification Search
CPC .............. A61B 1/00131; A61B 1/0014; A61B 1/00147; A61B 1/313
USPC .......................... 600/102, 104; 604/174, 177
See application file for complete search history.

(56) References Cited

U.S. PATENT DOCUMENTS

| 4,573,452 | A | 3/1986 | Greenberg |
| 5,147,373 | A | 9/1992 | Ferzli |
| 5,171,257 | A | 12/1992 | Ferzli |
| 5,201,759 | A | 4/1993 | Ferzli |
| 5,380,338 | A | 1/1995 | Christian |
| 5,441,042 | A * | 8/1995 | Putman .............. A61B 19/2203 600/102 |
| 5,779,623 | A | 7/1998 | Bonnell |
| 6,050,960 | A | 4/2000 | Ferzli |
| 7,413,543 | B2 | 8/2008 | Banik et al. |
| 7,955,275 | B2 | 6/2011 | Ferzli |
| 8,934,636 | B2 | 1/2015 | Ferzli et al. |
| 2003/0032922 | A1* | 2/2003 | Moorehead ....... A61M 25/0631 604/110 |
| 2005/0085689 | A1* | 4/2005 | Pagliuca ................ A61B 19/26 600/102 |
| 2006/0161136 | A1 | 7/2006 | Anderson et al. |
| 2006/0180714 | A1 | 8/2006 | Mailhot, Jr. |
| 2007/0185376 | A1 | 8/2007 | Wilson et al. |
| 2009/0299294 | A1 | 12/2009 | Pinkus |
| 2014/0200401 | A1 | 7/2014 | Ferzli |

OTHER PUBLICATIONS

Office Action mailed by the US Patent Office on Mar. 10, 2015 in the related U.S. Appl. No. 13/742,358.

* cited by examiner

*Primary Examiner* — Timothy J Neal
(74) *Attorney, Agent, or Firm* — Jordan and Koda, PLLC

(57) ABSTRACT

A coupling attachment includes a sleeve configured to at least partially surround a shaft or one or more other portions of a surgical instrument, such as a laparoscopic, during a surgical procedure. A grip is attached to the sleeve and used to hold the coupling steadily during the procedure.

12 Claims, 18 Drawing Sheets

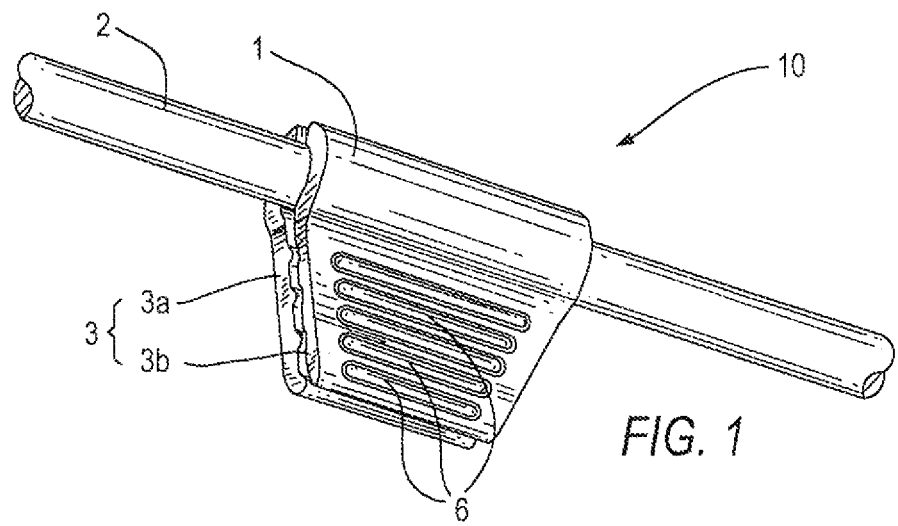
FIG. 1
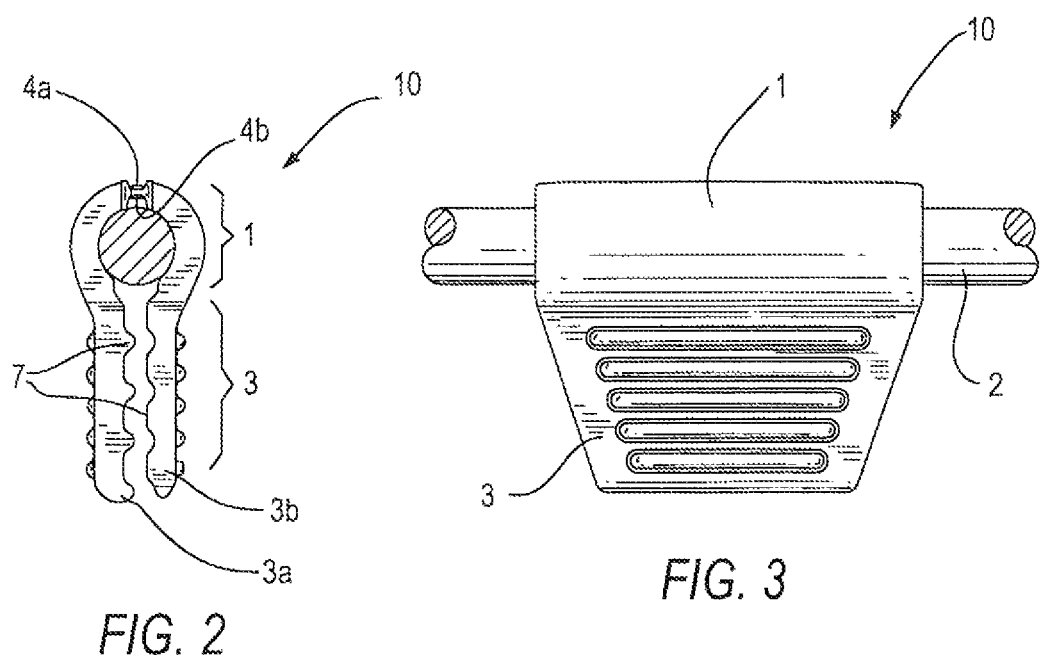
FIG. 2
FIG. 3

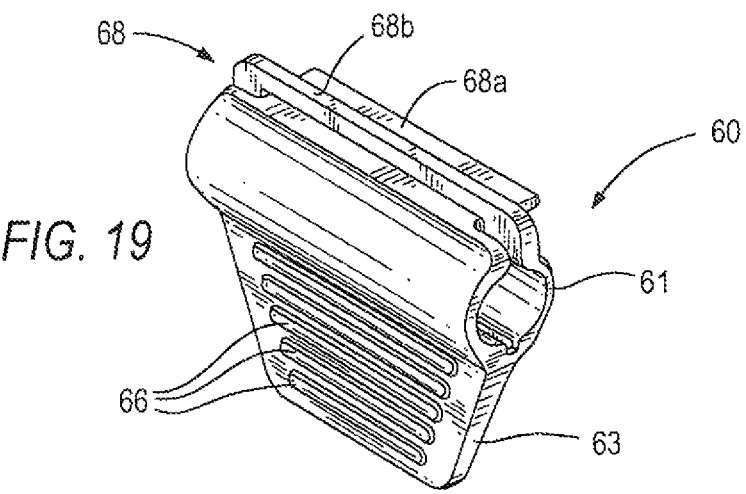
FIG. 19
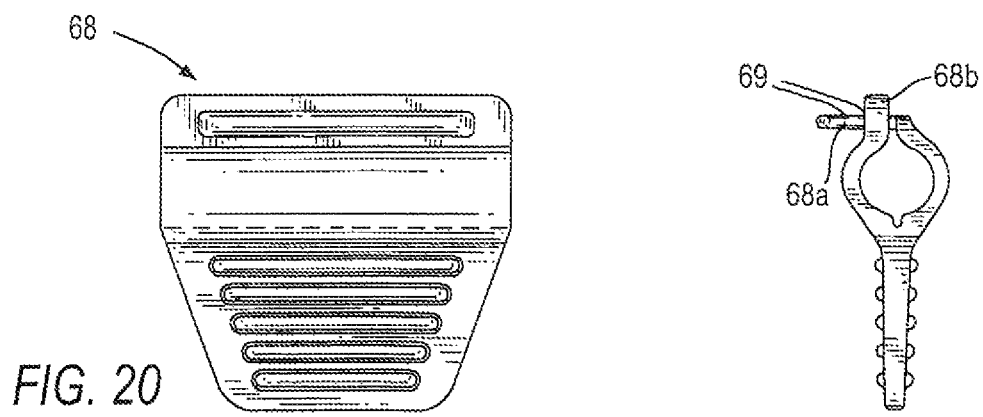
FIG. 20
FIG. 21
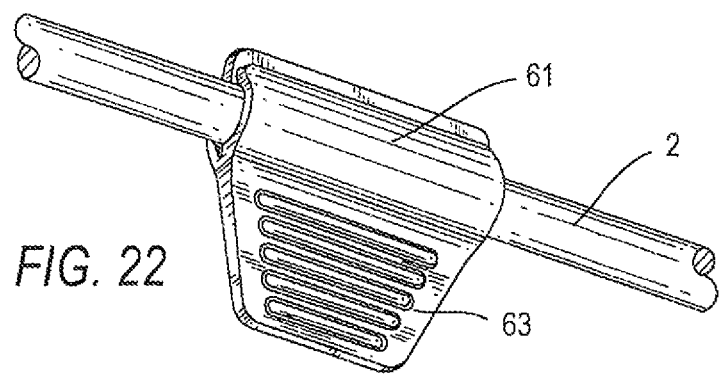
FIG. 22

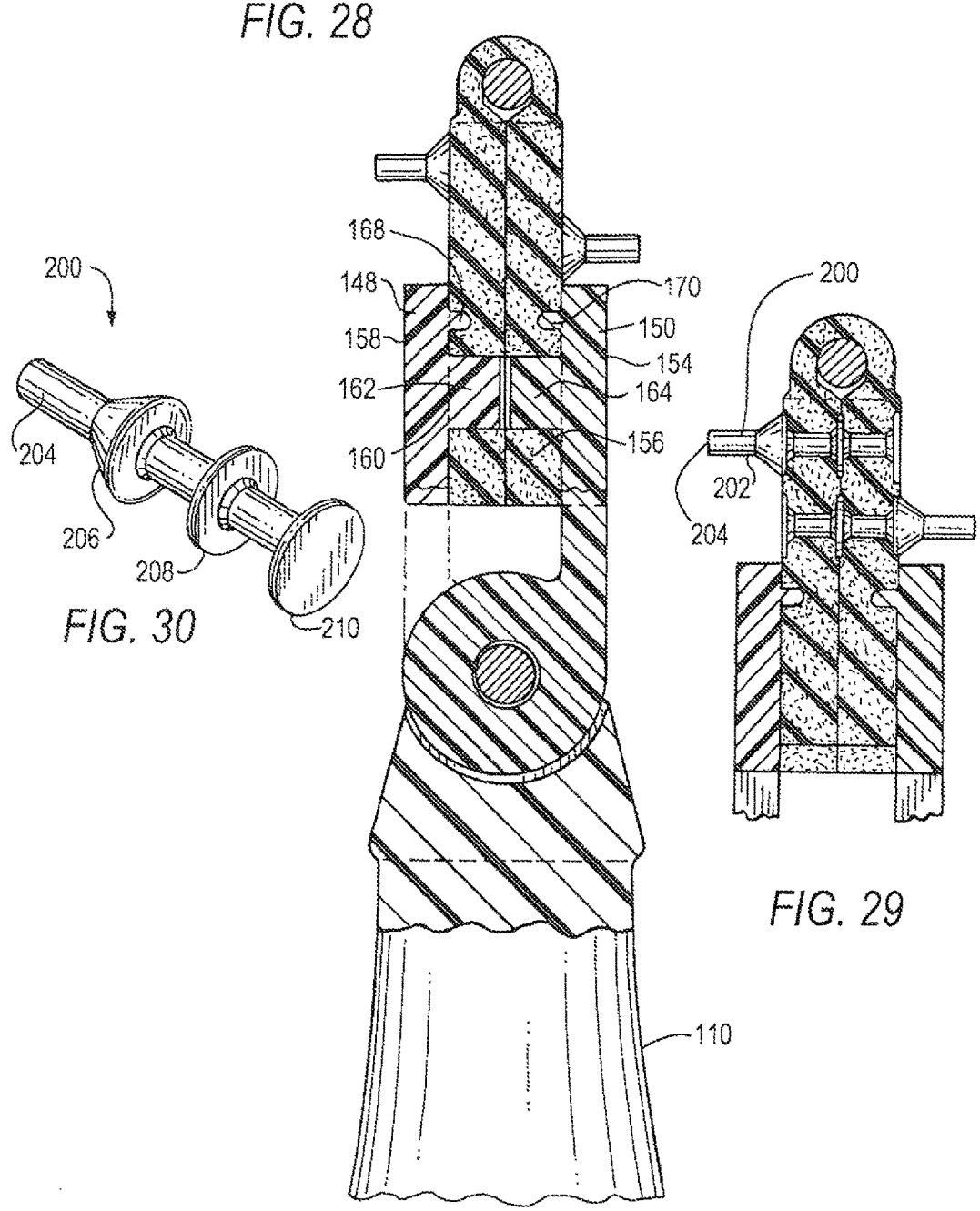

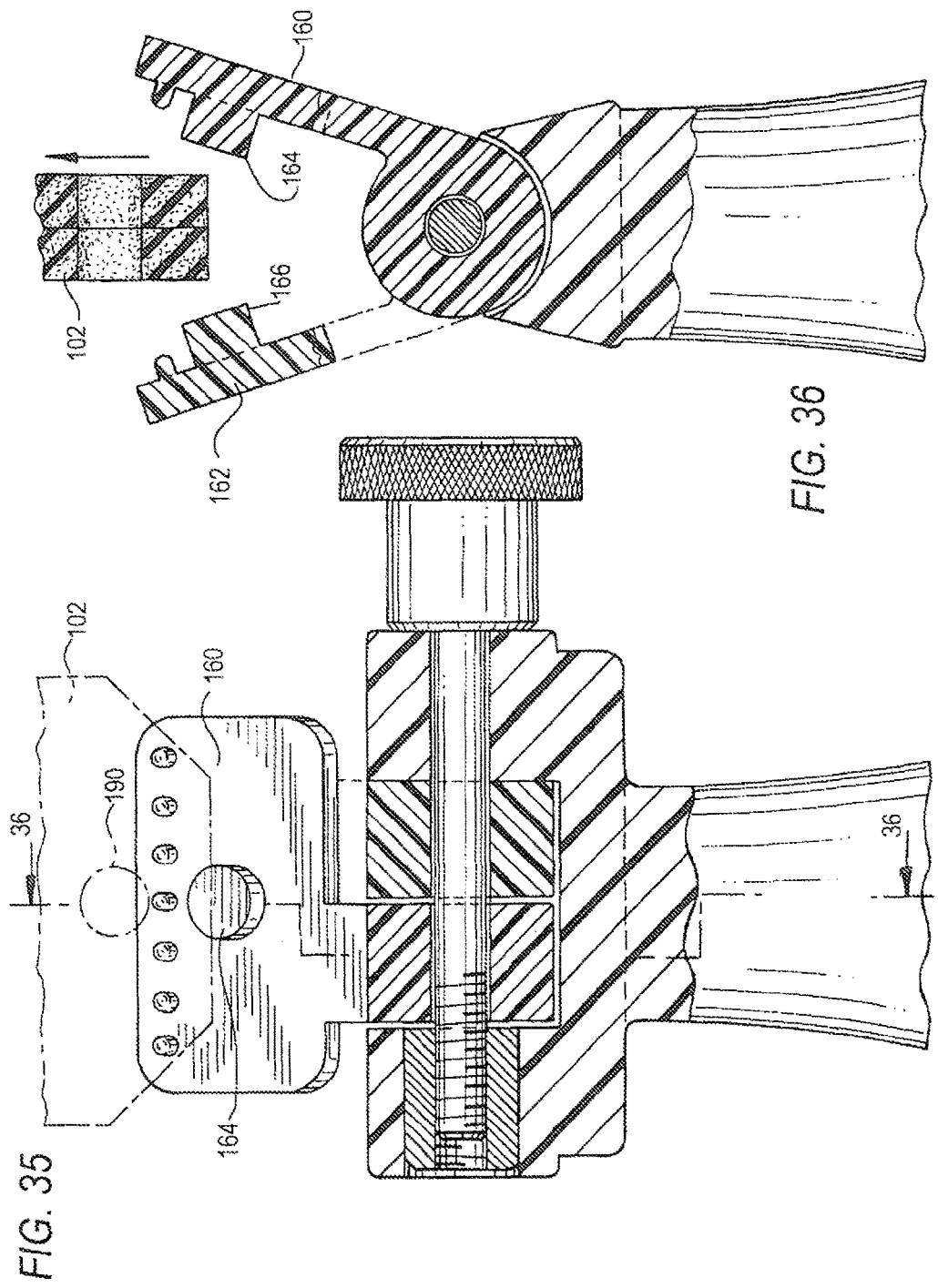

SUPPORT COUPLING FOR SURGICAL INSTRUMENT

RELATED APPLICATIONS

This application is a continuation-in-part of application Ser. No. 13/742,358 filed Jan. 16, 2013, claiming the benefit of U.S. Provisional Application No. 61/665,319 filed Jun. 28, 2012 all incorporated herein by reference in their entirety.

BACKGROUND OF THE INVENTION

The invention is directed to laparoscopic equipment, and more particularly to a coupling attachment which, when used in conjunction with laparoscopic instrumentation, facilitates the surgeon in the performance of laparoscopic procedures.

In order to perform a laparoscopic procedure, a camera is used to observe the interior of the patient so that proper surgical measures can be implemented by other types of equipment inserted inside the patent. During the laparoscopic surgery, according to conventional practice, the surgeon's assistant generally holds the camera head and guides the camera in, out, to the left, to the right, or rotates it as needed. This can be a tiring process and, as is often the case, the assistant experiences fatigue after holding the otherwise unsupported camera during prolonged surgery. Additionally, the assistant is commonly at risk of obstructing the working path of the surgeon. Several approaches have been suggested in the prior art to hold and positionally control laparoscopic instruments during surgery, in static, movable and robotic embodiments. When used in connection, for example, with laparoscopic cameras, each of these devices typically attach to the camera head. While conventional devices have addressed the need for providing mechanical assistance to the surgeon in controlling or maintaining the position of a laparoscopic camera during surgery, they are cumbersome to install, and each present potential drawbacks. For example, because of their size, conventional devices can obstruct the surgeon's working path, analogous with the problem frequently caused by a hand of an assistant. Although reusable, these existing devices are also expensive to initially purchase. They are complex to operate, requiring additional training and application steps during surgery. Expensive, reusable equipment, also requires post-surgery sterilization.

One example of such a conventional device is described in U.S. Pat. No. 5,779,623, in which a remote controlled "Positioner for Medical instruments" is described. It is complex, reusable and an expensive solution.

In US Pat. Pub. 2006/0161136, a "Surgical Accessory Clamp and System Method" is described. Such device similarly presents an Operating Room infrastructure solution with complex and expensive solutions for robotic instrument support.

No simple solution for positionally stabilizing and/or securing laparoscopic equipment has heretofore been suggested in either a disposable version, or in a compact and reusable form.

Furthermore, many of the conventional approaches fail to meet the basic need of simplifying the surgical operation, but instead introduce more complexity, and the potential of obstruction to the surgeon.

SUMMARY OF THE INVENTION

An object of the invention is to provide a coupling attachment that presents a relatively low cost, sterile solution to supporting and/or positionally maintaining laparoscopic surgical instruments/equipment and/or portions thereof, including, for example, laparoscopic cameras, during surgery.

The invention addresses these and other objects by providing a coupling attachment which, when engaged with a laparoscopic instrument or instruments or portions thereof, provides a convenient manner by which the laparoscopic equipment can be positionally supported or securably maintained, thereby providing a cost effective way to support the instrumentation, for example, a camera, during prolonged surgery or during times of potential interference from the camera operator with the working operation of the surgeon.

In an embodiment of the invention, the coupling attachment is engageably receivable to one or more laparoscopic surgical instruments, such as, for example, a camera, and includes a wing or other structural feature which is adapted to being securable by commonly used sterile surgical clamps (of which Ring forceps and Kelly clamps are examples). The various clamp attachment options present a convenient attachment and coupling method of the clamp to the surgical instrument.

In another embodiment, the coupling attachment is provided in the form of an elastic clip-on ring having a generally cylindrical inner bore in which a partial opening running in an axial direction of the coupling attachment in formed, which allows it to be pushed over a camera shaft, and the like. The inherent spring action in the elastically formed ring shape allows for a snap fit over the camera shaft, thereby maintaining same in removable captive engagement. This spring action is achieved through a function of geometric design, choice of material and/or manufacturing method, and by virtue of the further option of adding reinforcing stiffeners in the product during the manufacturing process. The finish to the inside of the ring, where it makes contact with the instrument shaft, will advantageously be sufficiently polished to ensure a snug fit, while also enabling rotation of the camera shaft, and axial movement of the clamped position to proximal and distal positions. This embodiment further supports the manufacturing of multiple ring sizes to accommodate leading contemporary instrument sizes, (for example, 2 mm, 5 mm, 7 mm, 10 mm, etc.) and can be easily adapted to any future size variations.

A further stabilization option exists to completely close the open end of the snap fit ring around the instrument shaft with a quick release buckle or strap fastener structural approach, that advantageously allows for easy operation.

In a particularly advantageous embodiment, the coupling attachment includes multiple position stabilization portions conveniently in the form of wings or other protrusions, that allow the coupling attachment to be grasped with a surgical clamp, for example, Ring forceps or a Kelly clamp). These clamps are present in all minor and major operating rooms, everywhere in the world. Advantageously, these protrusions should not bend excessively when the clamp is attached, for desired stability. Optional surface features on the wings (or protrusions) serving as position stabilization portions, provided in the form of ridging or other patterns, will advantageously enhance the clamp's grip.

Once clamped, the handle of the Kelly clamp or Ring forceps can rest on the operating field, thereby stabilizing the laparoscopic instrument connected thereto via the coupling attachment. Such connected arrangement would also have the ability to swing back and forth. The attached clamps can also be held by the surgical assistant, providing an alternative ergonomic handling solution, and has the potential to reduce fatigue during prolonged surgery. The surgeon would have the opportunity to attach multiple rings and clamps to the camera shaft, at both proximal and distal positions, creating a tripod support when rested onto the operation field.

The coupling attachment will advantageously be comprised of a relatively soft rubber, silicone, high-density foam material, or any other suitable material that is advantageously sterilizable if so desired, and that will not cause denting or damage to the camera or other instrument shaft, at least in regions of the coupling attachment that comes in contact therewith.

The specific nature of the material properties of each design is subject to the choice of embodiment pursued and manufacturing method employed. The coupling attachment is envisioned to optionally be disposable and affordable, offering a distinct economic benefit over existing solutions referenced in the prior art discussion above.

It is further envisioned, that an alternative embodiment of the same idea, could be achieved through creating a flat single part that folds over the shaft. This folding would be facilitated through the use of a flexible or living hinge, with clear geometric indicators allowing for the proper longitudinal alignment. The fold-over clamp attachment shares the properties of the ring embodiment, providing a rigid locked attachment for the surgical clamps, while allowing controlled movement and rotation on the camera shaft. The inner surface finish will be smooth, while the outer surface will have articulation to improve the grip area for the clamp. This embodiment allows for easy scaling of the manufacturing process to support multiple camera shaft diameters.

A further benefit derived from the coupling attachment according to the invention is that the device can be positioned to block the laparoscope against sliding into the abdomen. In some cases, efficient use may even negate the need for the surgical assistant.

In an embodiment directed to a method of using the coupling attachment according to the invention, the surgeon, or his/her assistant, can apply multiple coupling attachments to the shaft of the scope (camera) or other laparoscopic instrument. Two clamp attachments at different distances from each other may allow for the use of two different length clamps, as needed.

The option also exists to clamp the laparoscopic instrument to the operating field by using the coupling attachments according to the invention, and in doing so, further optimizing the surgical process. It is further envisioned that a thread with a radio-opaque marker could optionally be inserted into the coupling attachment during the manufacturing process, to ensure that the coupling attachments are always accounted for, in the event that a surgeon moves to open surgery due to an emergency mid-procedure.

In one embodiment, a coupling attachment for stabilizing a surgical instrument during a surgical procedure, said surgical instrument including a linear element, the coupling including a sleeve arranged and constructed for selective mounting on the linear element; and a grip including grip body sized and shaped to fit in a person's hand during the surgical procedure and mounting element attached to said body and arranged to secure said sleeve.

In one embodiment, the grip and the sleeve cooperate to define selectively a plurality of surgical procedure configurations, the linear element being supported at respective angle for each of said surgical procedure configurations.

In one embodiment, the sleeve is secured at a respective angle with respect to said grip for each of said surgical procedures.

In one embodiment, the sleeve is rotatable with respect to the grip.

In one embodiment, a coupling for holding a surgical instrument is presented in an optimal position during a surgical procedure, said surgical instrument including a shaft, said coupling including:

a sleeve made of a continuous elastomeric material and including two leaves connected by hinging element, said hinging element being arranged and constructed to wrap around the shaft and hold the shaft securely with said two leaves being disposed in an overlapping configuration; and a grip having a grip body having a cylindrical shape configured and sized to be held by a person during the surgical procedure and a mounting element attached to said grip body and arranged and constructed to selectively engage and secure immovably said leaves.

In one embodiment, the grip includes a pair of wings arranged and constructed to selectively engage and hold said sleeve by securing said leaves.

In one embodiment, The grip body defines a grip longitudinal axis and the wings are arranged and constructed to selectively pivot about a horizontal axis perpendicular to said grip longitudinal axis.

In one embodiment, a tightening element is mounted on said grip and arranged and constructed to tighten said wings in a predetermined position.

In one embodiment, the wings include a sleeve engaging member arranged and constructed to fixedly engage said sleeve.

In one embodiment, the sleeve includes leave securing elements for securing said sleeves together.

The above, and other objects, features and advantages of the present invention will become apparent from the following description read in conjunction with the accompanying drawings.

BRIEF DESCRIPTION OF THE DRAWINGS

FIG. 1 is a perspective view of a first embodiment of the coupling attachment according to the invention shown received on a shaft of laparoscopic instrument;

FIG. 2 is an end view of the first embodiment of FIG. 1;

FIG. 3 is a side view of the first embodiment of FIG. 1;

FIG. 19 is a perspective view of a sixth embodiment according to the invention which includes a clasp feature;

FIG. 20 is a side elevational view of the sixth embodiment;

FIG. 21 is an end view of the sixth embodiment;

FIG. 22 is a perspective view of the sixth embodiment shown received about a shaft of a laparoscopic instrument;

FIG. 28 shows a side elevational cross sectional view of the embodiment of FIG. 26;

FIG. 29 shows an enlarged side elevational cross sectional view of the embodiment of FIG. 26;

FIG. 30 shows an isometric view of a peg used in the embodiment of FIGS. 26-29;

FIGS. 35 and 36 show enlarged front and side sectional elevational views of the sleeve being inserted into the grip;

DETAILED DESCRIPTION OF THE PREFERRED EMBODIMENT

Figure 4:
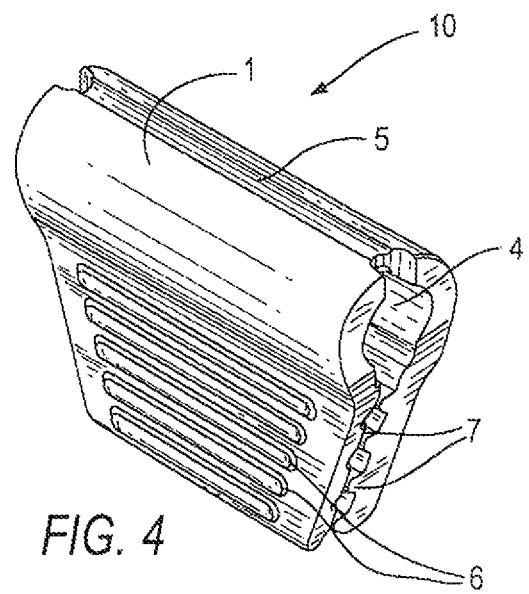
FIGS. 4 and 5 are perspective views of coupling attachments according to the first embodiment, sized to accommodate different diameter instrument shafts.

Before describing various depicted examples of different embodiments of the invention which will serve to illustrate, but not unnecessarily limit, the many ways in which the invention can be practiced without departure from the contemplated scope of the invention, the following broad considerations are outlined. In broad terms, a coupling attachment according to the invention is suitably configured to include a position stabilization portion and a laparoscopic instrument restraint portion, the latter which is configured to at least partially surround a shaft or one or more other portions of a laparoscopic instrument in a manner which positionally restrains or inhibits movement of the instrument and/or portion(s) thereof when the position stabilization portion is supportably engaged, for example, by a clamp or other form of securement. The support conveniently comprises the operating field on which, for example, a Kelly clamp, serving as the form of securement, is rested thereon (gravitational securement) or clamped thereto in addition to being clamped to the position stabilization portion of the coupling attachment (mechanical securement). Alternatively, the securement can be accomplished instead by any suitable method, for example, stitching a thread through the sheets of the operating field and through the position stabilization portion of the coupling attachment, by providing the coupling attachment with an outer sticky surface having a release tape that could peel off allowing the coupling to stick to the drapes of the operating field, etc.

For purposes herein, the term "laparoscopic instrument" or "laparoscopic equipment" is defined to include any and all devices used in laparoscopic surgery or procedures, and not exclusively the laparoscope (i.e. camera) itself. These will include, but not be limited to, portions or entireties of one or more of the following examples: a camera connected with a cord to a tower distant from the operating field, a grasper, a dissector, a retractor, a light cord cable, insufflator tubing, cautery cords connected to a power generator, ultrasonic device (eg., harmonic, ligasure) connected with a cord to the power generator, a suction irrigation device connected with two tubings to the ceiling and a collection canister, additional tubing for the regular suction, a bipolar cord, a laser cord, etc.

Referring now to the figures, and in particular FIGS. 1-5, a first embodiment of a coupling attachment is depicted in various views, and is generally designated by the numeral 10. Coupling attachment 10 includes a laparoscopic instrument (or other surgical instrument) restraint portion 1 which is configured to at least partially surround a camera shaft 2 and a position stabilization portion 3 for attachment of a securement device, for example, a conventional clamp (not shown). In the depicted example, position stabilization portion is comprised of a pair of wings 3a, 3b extending from the centrally located instrument restraint portion 1, and which are brought into facing positions when the coupling attachment 10 is received about the camera shaft 10. Coupling attachment 10 is comprised of an elastomeric material which allows at least sufficient deformation thereof to permit its installation about a camera shaft 2. While camera shaft 2 is used for illustration purposes, it will be understood that coupling attachment 10 will find utility for use with virtually any type of laparoscopic instrument designed for partial introduction into a patient's body.

Coupling attachment 10 can be manufactured either in a generally flattened shape when unstressed (not shown in FIGS. 1-5, but can be seen in an alternative embodiment of FIGS. 12-14), in which case the coupling attachment 10 is folded around the camera shaft 2 and the pair of wings 3a, 3b then being held together by a clamp (not shown) which secures the coupling attachment 10 to the camera shaft 2, or alternatively can assume the shape as shown in FIGS. 1-5 in a resting state, in which case the pair of wings are simply spread apart to receive the camera shaft 2 within the internal receiving channel 4 of the laparoscopic instrument restraint portion 1. Particularly in the case in which coupling attachment 10 assumes a flatted shape in its natural state, axially extending indentations 4a, 4b of generally flat configuration along a center hinge line 5 are advantageously provided to allow for quick visual alignment during the folding-over of coupling attachment 10 about camera shaft 2.

Figure 5:
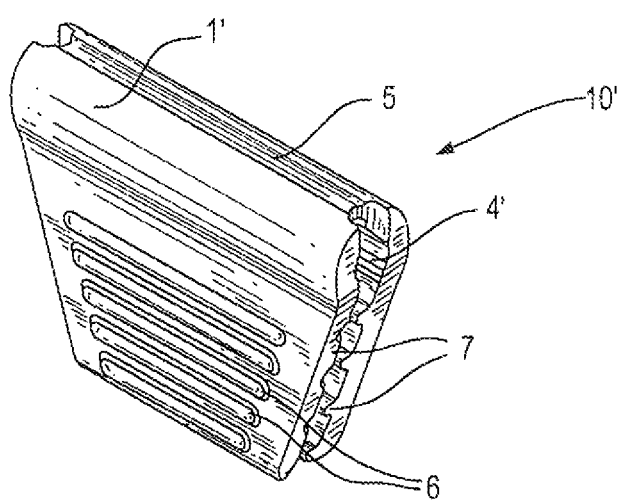
Figure 6:
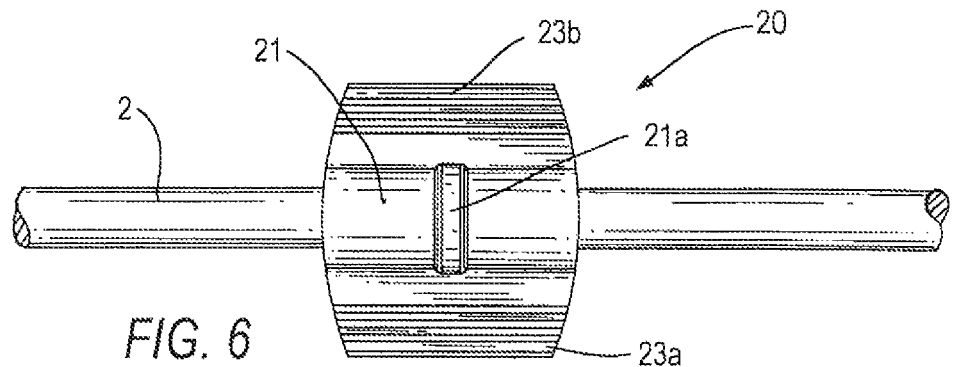
FIG. 6 is a top plan view of a second embodiment of the invention.
Figure 7:
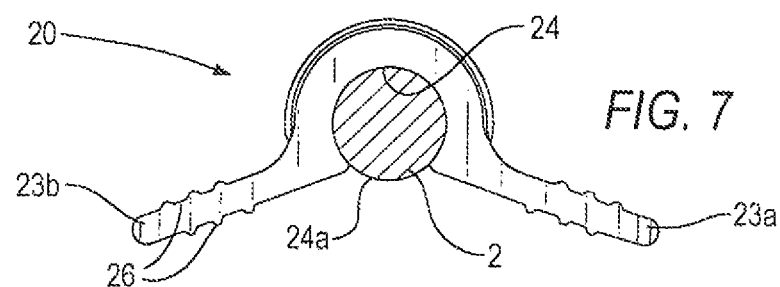
FIG. 7 is an end view of the second embodiment.

Raised surface ridges 6 are advantageously provided on the outward facing surfaces of the on pair of wings 3a, 3b, operate to enhances the gripping region for the attachable clamp. Additionally, optional teeth 7 further enhance the part closure and rigidity of coupling attachment 10, while allowing for controlled axial movement or rotation along the camera shaft 2. In addition to the version of coupling attachment 10 shown in FIG. 4 having an internal receiving channel 4 adapted to a shaft diameter of the camera shaft 2, as shown in FIGS. 1-3, an alternatively sized coupling attachment 10' is shown in FIG. 5, having a internal receiving channel 4' of smaller diameter which is configured to receive a shaft (not shown) of smaller diameter, for example, that of a laparoscopic retractor.

Turning now to FIGS. 6-10, a second embodiment of a coupling attachment according to the invention is depicted, generally designated by the numeral 20. Coupling attachment 20 is provided in the form of an elastic clip-on ring including a laparoscopic instrument restraint portion 21 having a generally cylindrical inner bore 24 in which a partial opening 24a running in an axial direction of the coupling attachment 20 is formed, allowing it to be pushed over a camera shaft 2. The inherent spring action attendant the elastically formed ring shape allows for a snap fit over the camera shaft 2, thereby maintaining same in removable captive engagement. This spring action is achieved through a function of geometric design, choice of material and/or manufacturing method, and the further option of adding reinforcing stiffeners in the product during the manufacturing process. The finish to the inside of the of the cylindrical inner bore 24, where it makes contact with the camera shaft 2, will advantageously be sufficiently polished to ensure a snug fit, while also enabling rotation of the camera shaft 2, and axial movement of the clamped position to proximal and distal positions, it is reiterated that this invention need not be limited to a camera shaft 2, which is only being used herein for illustration purposes.

Coupling attachment 20 includes a pair of position stabilization portions conveniently provided in the form of wings 23a, 23b which extend bilaterally from laparoscopic instrument restraint portion 21. Raised surface ridges 26 are advantageously provided on the outward facing surfaces of the pair of wings 23a, 23b, and operate to enhance the gripping region for a clamp (not shown).

Figure 8:
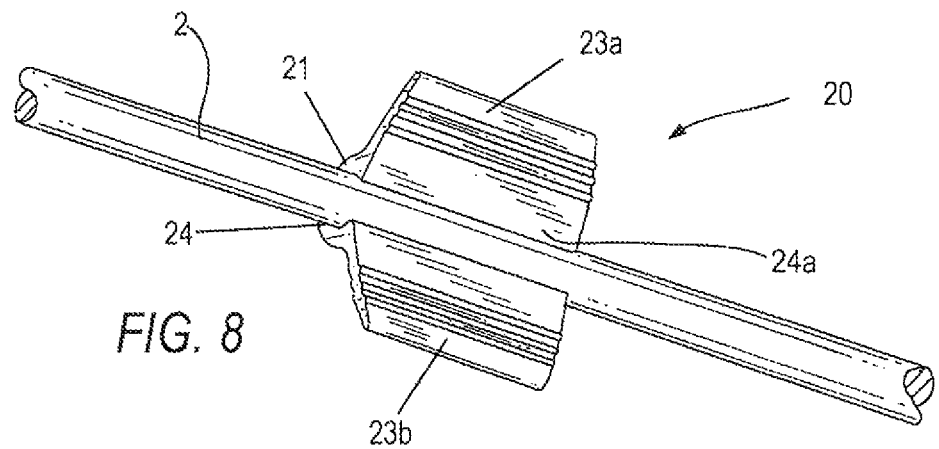
FIG. 8 is an underside perspective view of the second embodiment.
Figure 9:
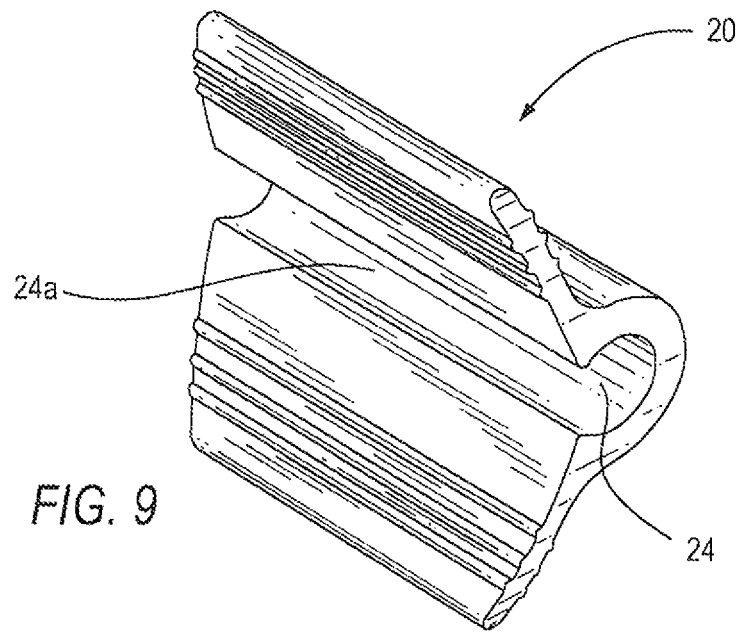
FIGS. 9 and 10 are perspective views of coupling attachments according to the second embodiment, sized to accommodate different diameter instrument shafts.
Figure 10:
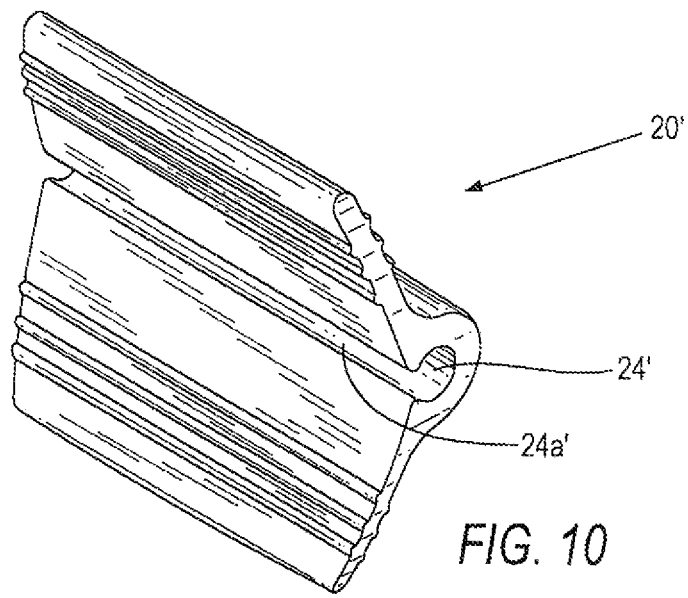

FIG. 8 is a perspective view of the coupling attachment 20 clipped onto camera shaft 2. A reinforcement ridge 21a is optionally provided on the outward facing surface of the laparoscopic instrument restraint portion 21 which includes the cylindrical inner bore 24, designed to keep the attachment stable at a constant tension and position unless moved by the user.

The second embodiment also optionally allows for variations with one, three, four or more wings rather than the pair of wings 23a, 23b as shown. The dimensions of coupling attachment 20 readily scale to support instruments with different shaft diameters, and shown, for example, in FIG. 10, in which a coupling attachment 20' has a cylindrical inner bore 24' suited for a smaller diameter instrument shaft, such as that of a retractor.

Figure 11A:
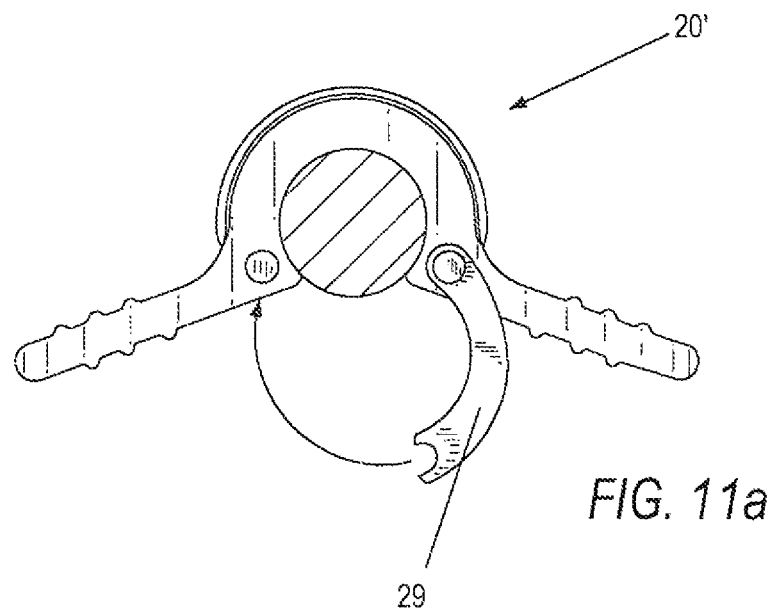
FIGS. 11A and 11B are end views depicting a third embodiment of the coupling attachment according to the invention shown in open and locked positions, respectively.
Figure 11B:
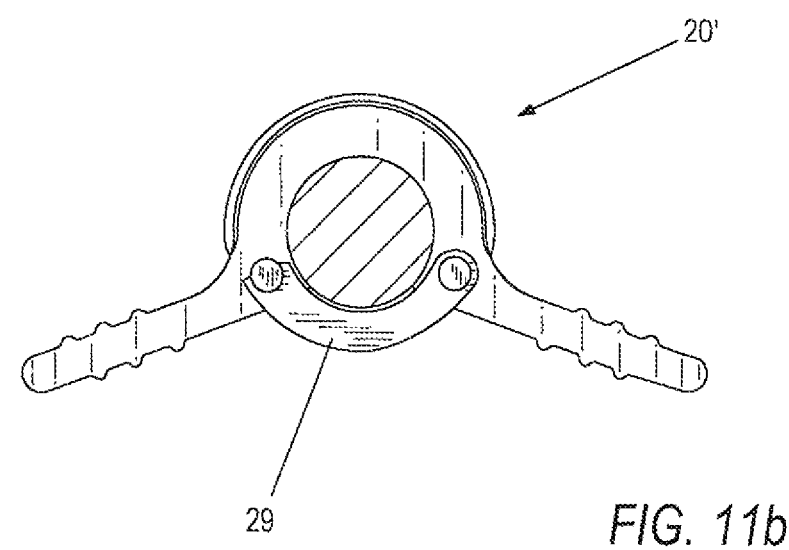

Turning now to FIGS. 11a and 11b, a third embodiment of a coupling attachment is depicted, which is a modified version of the second embodiment described above, and is generally designated by the numeral 20'. As depicted in cross sectional views, the second embodiment is modified by the optional provision of a clasp 29 which provides further stabilization for secured retention to the instrument shaft (e.g., camera shaft 2), by completely closing the open end of the snap fit ring around the camera shaft 2 which would operate as a quick release buckle or strap fastener type structural mechanism, advantageously allowing for easy operation.

Figure 12:
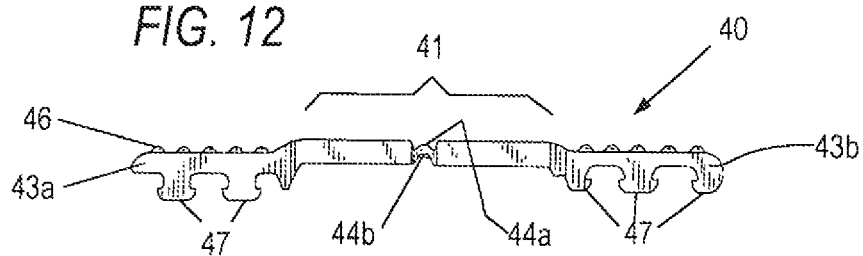
FIG. 12 is a side elevational view of a fourth embodiment according to the invention to a fold-over version which includes interlocking teeth.
Figure 13:
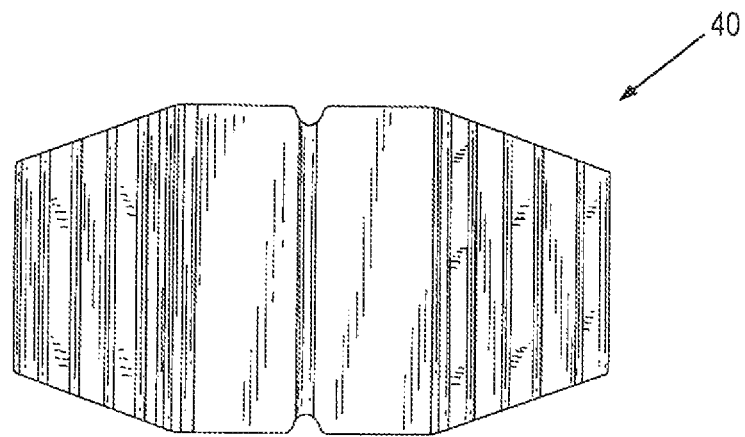
FIG. 13 is a top plan view of the fourth embodiment of FIG. 12.
Figure 14:
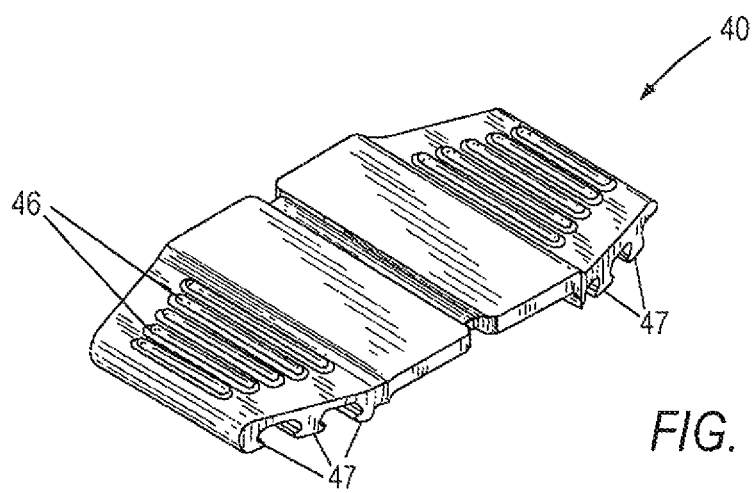
FIG. 14 is a perspective view of the fourth embodiment.
Figure 15:
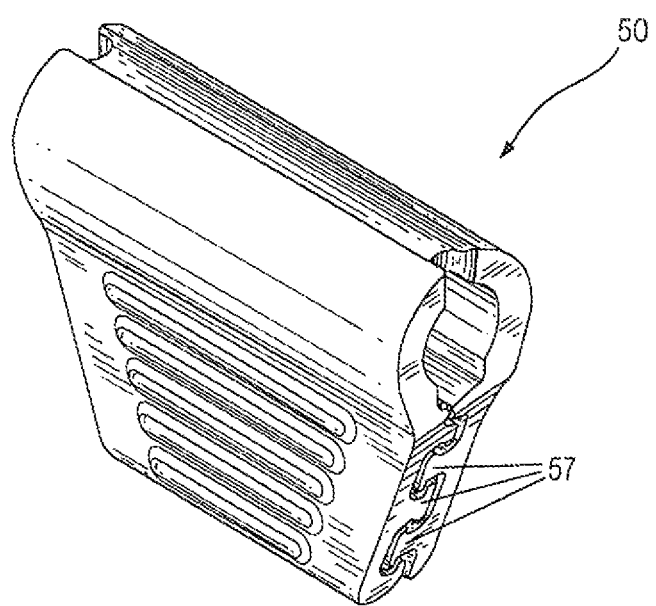
FIG. 15 is a perspective view of a fifth embodiment which includes interlocking teeth.

Referring now to FIGS. 12-14, a fourth embodiment of a coupling attachment is depicted generally at 40. Coupling attachment 40 includes analogous structural features with the first embodiment of FIGS. 1-3, including a laparoscopic instrument restraint portion 41 which is configured to at least partially surround a shaft (not shown) and a position stabilization portion for attachment of a securement device comprised of a pair of wings 43a, 43b extending from the centrally located instrument restraint portion 41, and which are brought into facing positions when the coupling attachment 40 is received about the instrument shaft. Coupling attachment 40 is comprised of an elastomeric material which is sufficiently flexible to be conformably bent from is normally flat shape, as shown, to wrap around the instrument shaft. Axially extending indentations 44a, 44b of generally flat configuration along a center hinge line 5 are advantageously provided to allow for visual alignment during the folding-over of coupling attachment 40 about the instrument shaft.

As with the first embodiment, raised surface ridges 46 are advantageously provided on the outward facing surfaces of the on the on the pair of wings 43a, 43b, operate to enhances the gripping region for reception of the clamp. Instead of providing the optional teeth 7 as shown with reference to the example of the first embodiment of FIGS. 1-3, the fourth embodiment as shown in FIGS. 12-14 provides the particularly advantageous feature of interlocking teeth 47 which are shaped to not just align, as in the first embodiment, but additionally to pressure fit, so that they stay interlocked, even without an attached clamp (Kelly clamp or the like). This removes the need to use a second hand to keep coupling attachment 40 in place after removing the clamp, and eases the movement axially along the instrument shaft after removal of the clamp.

The above feature is considered to be particularly advantageous since, as is often the case during surgery, the laparoscope has to be removed from the abdomen of the patient to have the lens cleansed before replacing it into the abdomen. Without the feature described above (or other alternative structural provision which maintains the closure of coupling attachment 40 about the instrument shaft and the secured engagement of the coupling attachment thereto) it is either necessary to remove the clamp, which would cause the coupling attachment to be dropped or flung onto the operating field, and later require it to be located to replace it on the shaft, or move the entire scope/coupling attachment/clamp as an attached unit, which is cumbersome and not particularly desirable. The above feature obviates these undesirable options, since upon removal of the laparoscope from the abdomen, the clamp is removed and the coupling attachment 40 remains securely in place, to be re-gripped with the clamp once the laparoscope is returned to the abdomen.

Figure 16:
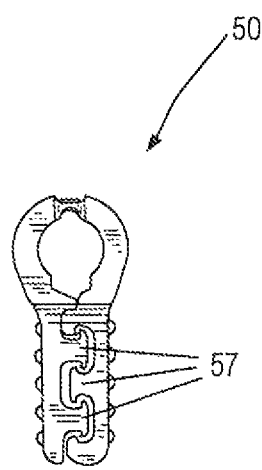
FIG. 16 is an end view of the fifth embodiment.
Figure 17:
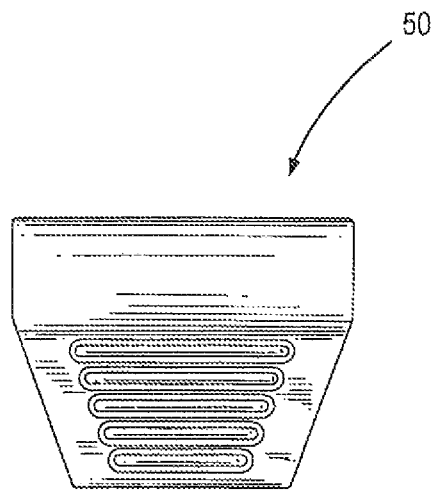
FIG. 17 is a side elevational view of the fifth embodiment.
Figure 18:
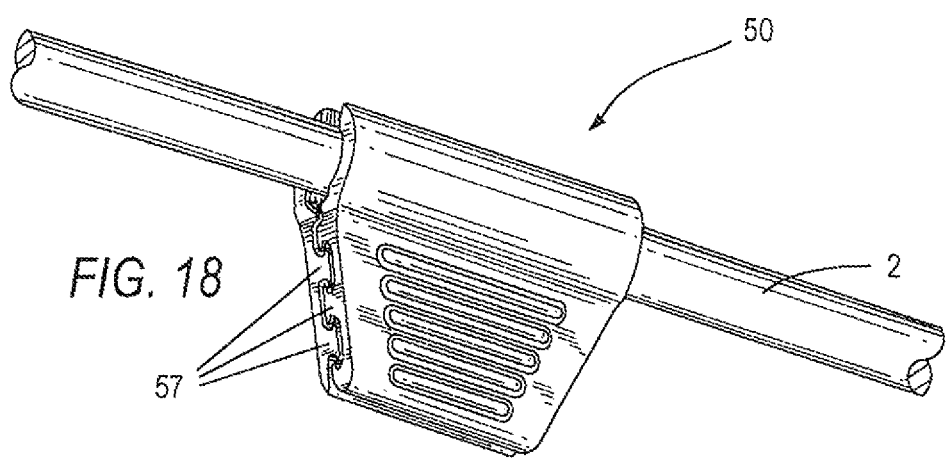
FIG. 18 is a perspective view of the fifth embodiment shown received about a shaft of a laparoscopic instrument.

Referring to FIGS. 16-18, a fifth embodiment of a coupling attachment according to the invention is designated generally by the numeral 50. The fifth embodiment is in all respects analogous with the first embodiment of FIGS. 1-5, and as such, description their shared features is omitted as being redundant.

The fifth embodiment of FIGS. 16-18, like the fourth embodiment, replaces the optional teeth 7, as shown with reference to the example of the first embodiment of FIGS. 1-3, with interlocking teeth 57 which are shaped to not just align, as in the first embodiment, but to pressure fit so that they stay interlocked, even without an attached clamp. These provide the same advantages as those described above with reference to the fourth embodiment of FIGS. 12-14.

As discussed above, many structural approaches can be used in place of the interlocking teeth described with reference to the fourth and fifth embodiments in order to maintain secure retention of coupling attachment about the instrument shaft and achieve analogous function. One such alternative approach is shown, by example, with reference to a sixth embodiment, shown in FIGS. 16-18.

Turning to FIGS. 19-22, a coupling attachment according to the sixth embodiment is depicted, designated generally by the numeral 60. Coupling attachment 60, which like the other embodiments is comprised of a material exhibiting elastomeric properties, includes a laparoscopic instrument restraint portion 61 which is configured to at least partially surround a camera shaft 2 (see FIG. 22) and a position stabilization portion 63 for attachment of a securement device, for example, a conventional clamp (not shown). Rather than being comprised of a pair of wings as in the first embodiment, position stabilization portion is comprised a single wing 63 extending from the instrument restraint portion 61.

As with the previously described embodiments, raised surface ridges 66 are advantageously provided on the outwardly facing surfaces of the wing 63 for improved gripping by a clamp.

In the sixth embodiment, a top edge of the laparoscopic instrument restraint portion 61 is open and is modified to define a clasp mechanism 68. The clasp mechanism is comprised of a strap 68a and a slotted buckle 68b combination, in which the strap 68a is kept in place by friction through a series of ridges 69 on the outer surface of the strap 68a.

Figure 23:
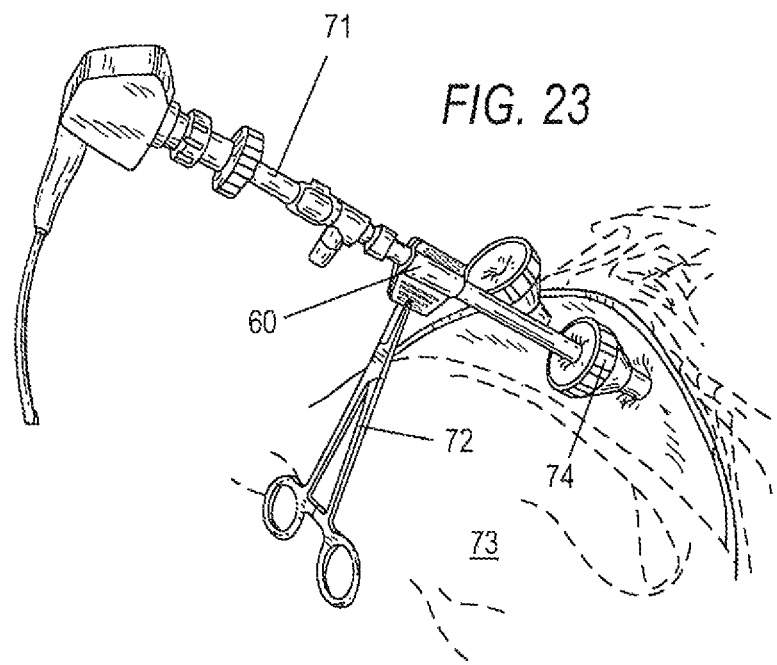
FIG. 23 is an explanatory view of the coupling attachment according to an embodiment of the invention received to a laparoscopic instrument shaft allowing stabilization of the instrument by a clamp resting on the operative field.
Figure 24:
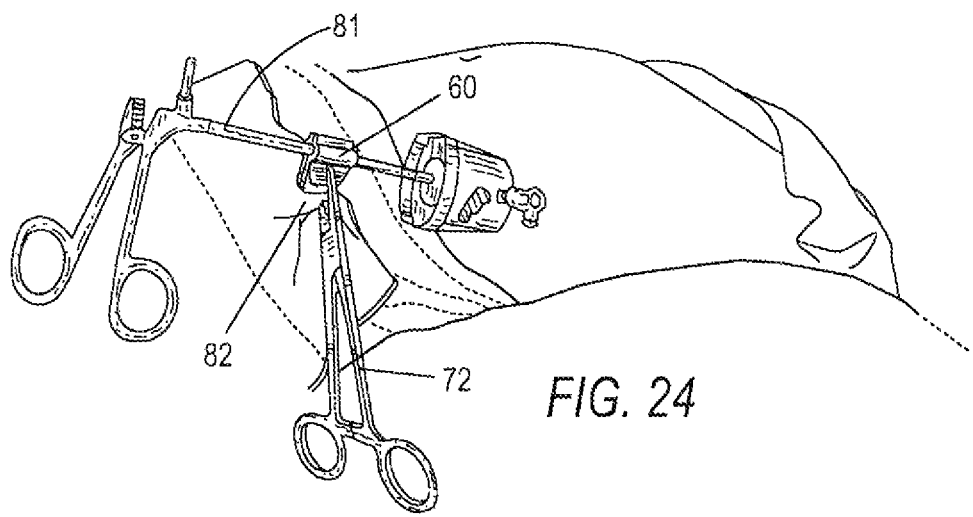
FIG. 24 is an explanatory view of a coupling attachment according to an embodiment of the invention received to a laparoscopic instrument shaft allowing stabilization of the instrument by a clamp resting on the operative field and which is also clamped to the operative field.
Figure 25:
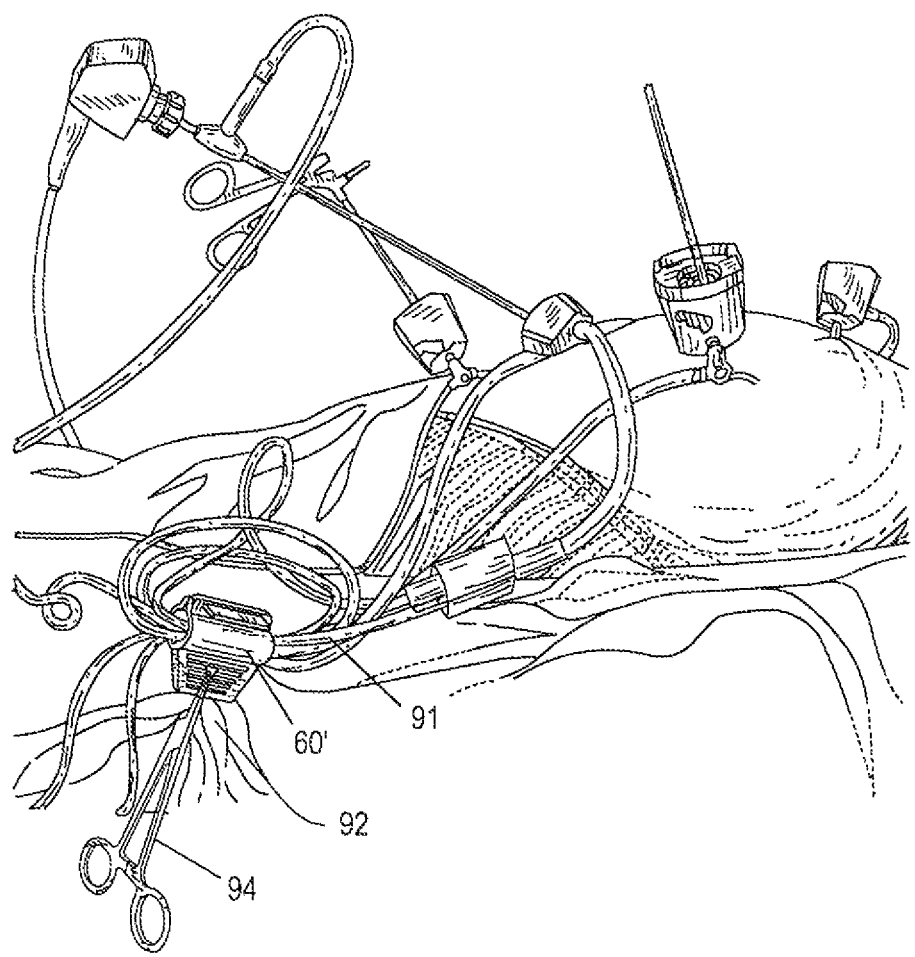
FIG. 25 is an explanatory view of a coupling attachment according to an embodiment of the invention used to organize and positionally maintain multiple 5 portions of laparoscopic equipment.

Turning now to FIGS. 23-25, various methods of use for the coupling attachment according to the invention are depicted.

FIG. 23 depicts a surgery in progress, with a laparoscopic camera 71 being supported by a Kelly clamp 72 attached to coupling attachment 60 (sixth embodiment) clipped over the camera shaft 71. The Kelly clamp 72 rests on the operating field 73. The combination of the camera 71 at its junction with trocar 74 and the handle of the Kelly clamp 74 provides gravitational support in the nature of a tripod.

FIG. 24 depicts another surgical use for the coupling attachment of the invention. As shown, in use in a laparoscopic cholecystectomy, a grasper 81 that is retracting the liver of a patient, is anchored to the operating table sterile cover using the coupling attachment 60, by placing the coupling attachment on the shaft of the grasper 81 or on the handle of the instrument, and then using a Kelly clamp 72 to grasp the coupling attachment 60 along with the surgical field drapes 82 of the operating table sterile cover. As such, the field drapes 82 serve to securely anchor the grasper 81.

Referring to FIG. 25, a surgical procedure is illustrated in which the coupling attachment according to the invention is shown used to organize as positionally support various laparoscopic instruments and portions thereof.

During laparoscopic surgery the following instruments/equipments are routinely used: a camera connected with a cord to a tower distant from the operating field, a light cord cable connected to the same tower, insufflator tubing connected to the same tower, two cautery cords connected to a power generator, an ultrasonic device (e.g., Harmonic, Ligasure) connected with a cord to the power generator, a suction irrigation device connected with two tubings to the ceiling and the collection canister, occasionally an additional tubing for the regular suction, a bipolar cord, a laser cord, etc. Consequently, there are at a general minimum, seven cords/tubings, crossing from the operating field to remote devices (power generators etc.) Occasionally, there are sometimes even ten of them.

FIG. 25 illustrate a larger dimensioned coupling attachment around all the various cords and tubes 91 along their course. Although one is shown, several similar coupling attachments can also be used. This embodiment directed to a method of use, allows the nurse/resident/surgeon to affix cords and tubes neatly to the surgical field. The coupling attachments is shown anchored to the surgical field drapes 92 with a surgical clamp 94.

It is noted that although the coupling attachment in accordance with the invention is described as being independent of a clamp which is subsequently attached to the position stabilization portion of the coupling attachment to provide support, it is contemplated that the coupling attachment according to another embodiment, deemed within the scope of the invention, can include independent support structure integral with, or assembled to as part of, the position stabilization portion, so as to obviate the need for an external clamp separate of the coupling attachment. For example, as mentioned above, the integrated support structure can be no more than a self-sticking adhesive included on the position stabilization portion, protected by a release film which, when removed, allows adhesion to a support surface, such as the drapes of the operating field. Alternatively, the position stabilization portion can be made in a form of a modified wing which extends a sufficient distance, or extendable by an adjustable distance, from the laparoscopic instrument restraint portion, and having a suitable terminal end shape and size, so as to serve as its own support when rested atop the operating field.

As can be seen in FIGS. 23-25, it has been envisioned that the couplings described previously are held via a Kelly clamp, such clamp 94. However, couplings can also be provided for supporting various surgical instruments, said couplings being supported with their grip that is sized and shaped to fit into a surgeon's or assistant's palm. Such a grip is advantageous because it is easier to hold for an extended period of time. Moreover the coupling with the grip could be made from elastomeric materials that could be rendered antiseptic, or could be made from cheap materials to render them disposable.

Figure 26:
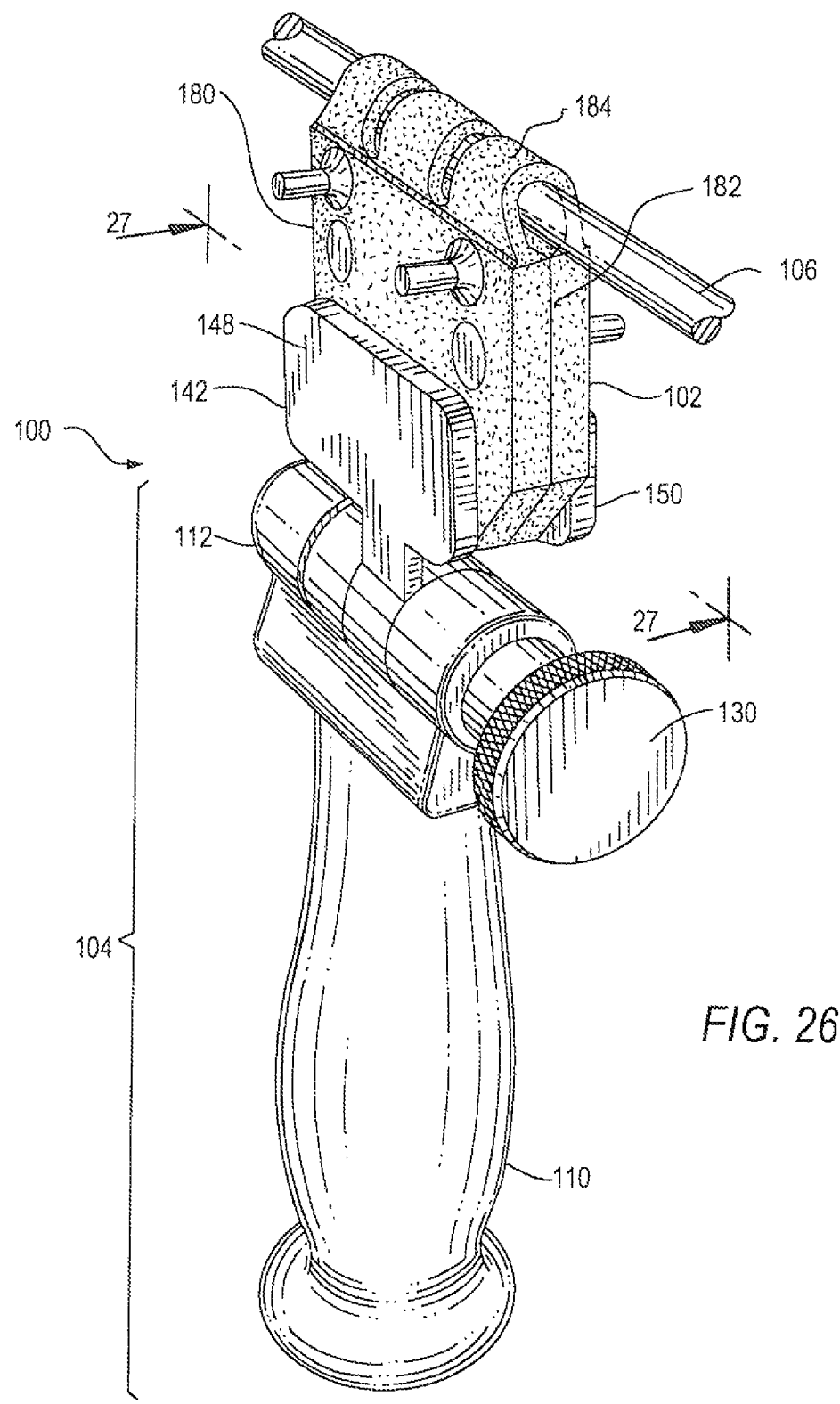
FIG. 26 shows an alternate embodiment of the invention.
Figure 27:
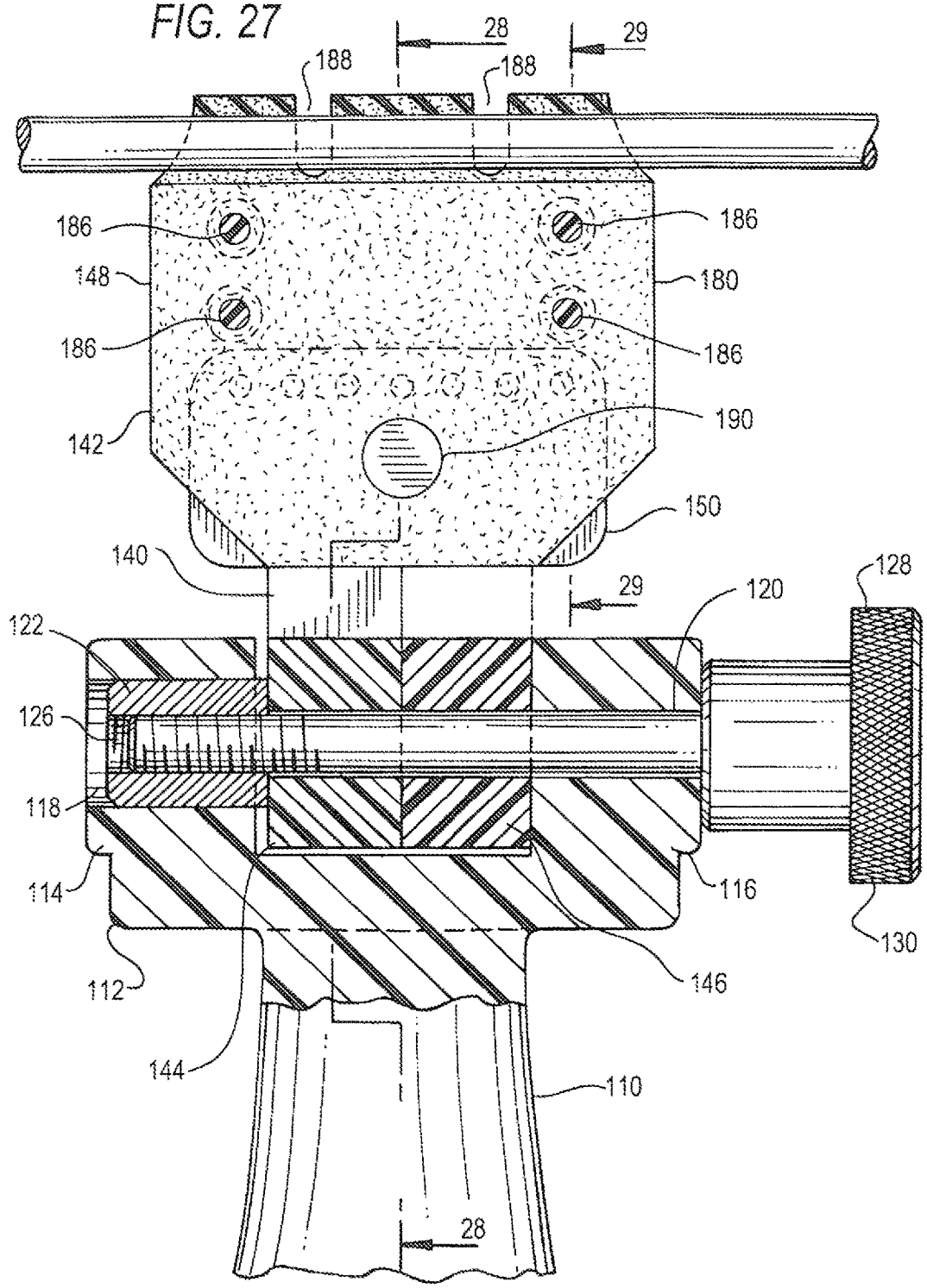
FIG. 27 shows a front elevational cross sectional view of the embodiment of FIG. 26.
Figure 31:
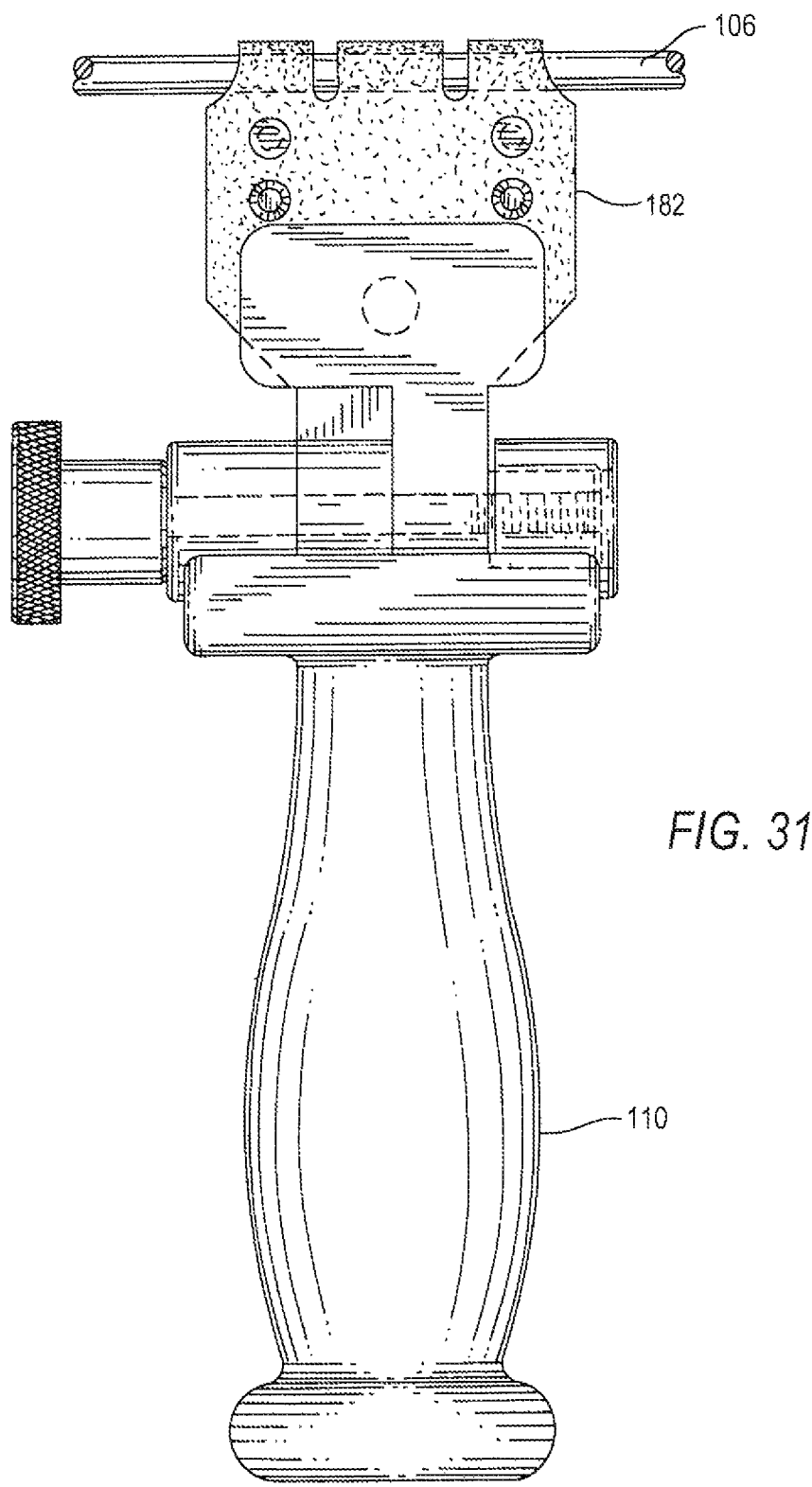
FIG. 31 shows a front elevational view of the embodiment of FIG. 26.

For example, as shown in FIG. 26—another embodiment of a support coupling 100 includes a sleeve 102 and a grip 104. The sleeve 102 is made of a soft elastomeric material that is easy to bend and easy to sterilize. As described in more detail below, it is constructed and arranged to wrap around an elongated portion 106 of a surgical tool. The surgical tool may be any of the tools discussed above illustrated in FIGS. 23-25. The grip 110 can be made by molding or other well known means, preferably from a high impact plastic material, except as noted below.

Grip 104 includes a lower handle 110 having a generally cylindrical shape and a head 112 extending generally horizontally to form a T with the handle 110. The head 112 includes two end bosses 114, 116, each having through hole 118, 120. Through hole 118 holds a threaded metal sleeve 122 fixed within the hole 118 so that the sleeve 122 cannot turn. A screw 124 extends from through hole 120 to the sleeve 122 and is provided with a threaded end 126 engaging the metal sleeve 122. The other end of screw 124 has a screw head 128 with a knurled annular wall 130 that facilitates turning the screw 124.

Grip 104 further includes two flaps 140, 142. Each flap 140, 142 includes a respective hollow round boss 144, 146. The hollow bosses 144, 146 are disposed between the end bosses 114, 116 and the screw 120 passes through the hollow bosses 144, 146. The grip 104 is made of a plastic material that is slightly flexible so that tightening the screw 120 to sleeve 122 causes the end bosses 114, 116 to flex toward each other axially to pinch the bosses 144, 146 of flaps 140, 142. In other words, when the screw 120 is loose, the flaps 140, 142 are free to rotate about the screw 120. When the screw 120 is tightened, the flaps are immobilized and cannot rotate.

Each of the flaps further includes a generally flat rectangular portion 150, 152. Flap portion 148 has an outer surface 158 and an inner surface 160 and flat portion 152 has an outer surface 154 and an inner surface 156 as shown in FIG. 30. The inner surfaces 156 and 158 further include round bosses 162, 164 respectively. In addition, or instead of the bosses 162, 164, the inner surfaces include several small teeth or spikes 168, 170 as shown.

As mentioned before, sleeve 102 is made of a relatively flexible material such as an elastomeric composition, and includes two identical leaves 180, 182 joined by a hinging section 184. Each leaf is provided with a plurality of through holes 186, In the figures the leaves 180, 182 are shown with four such holes 186, it being understood that more or less number of holes may be provided as well.

The hinging section 184 is somewhat thinner than leaves 180, 182 to facilitate wrapping the section 184 around the shaft 106. Further flexibility to hinging section 184 is provided by a pair of slits 188.

Finally, each leaf is provided with a central hole 190. These central holes 190 have the same, or a slightly smaller diameter then bosses 162, 164.

Finally, a plurality of pegs 200 are provided. The purpose of these pegs is to hold the two leaves 180, 182 in contact with each other in a juxtaposed orientation. For this purpose, each peg 200 includes a central shaft 202 having a uniform cylindrical shape (See FIG. 30), a head 204, a circumferential rib 206, a central disc 208 and an outer disc 210.

The coupling 100 is used as follows. The pegs 200 are inserted either before into one of the leaves 180, 182 as part of the installation of the coupling 100. The leaves are positioned over the shaft 106 of a surgical instrument with the hinging section 184 extending about and the shaft as shown. The two leaves 180, 182 are then secured to each other by passing the pegs through the holes 186. In their final position, the pegs 200 extend between the leaves through their holes 186 as shown in the figures. Up to four pegs 200 may be used, preferably in a staggered configuration so that two of the pegs 200 have their respective heads 204 disposed on side of the two leaves and the other two are disposed on the other side of the leaves.

Figure 33:
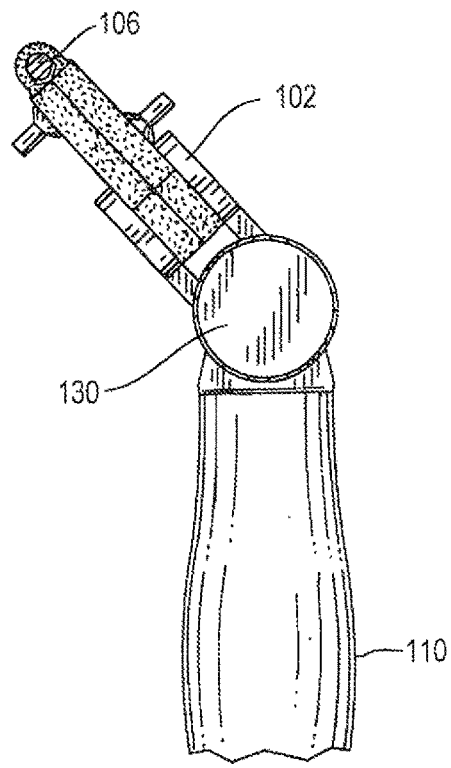
FIGS. 32, 33 and 34 show side elevational views of the embodiment of FIG. 26 with the sleeve being disposed at various angles with respect to the grip for various surgical procedures.
Figure 32:
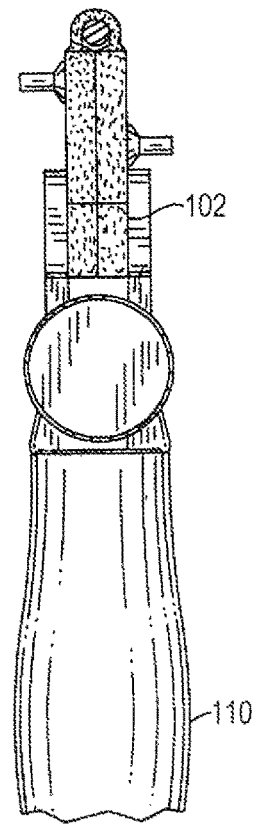
Figure 34:
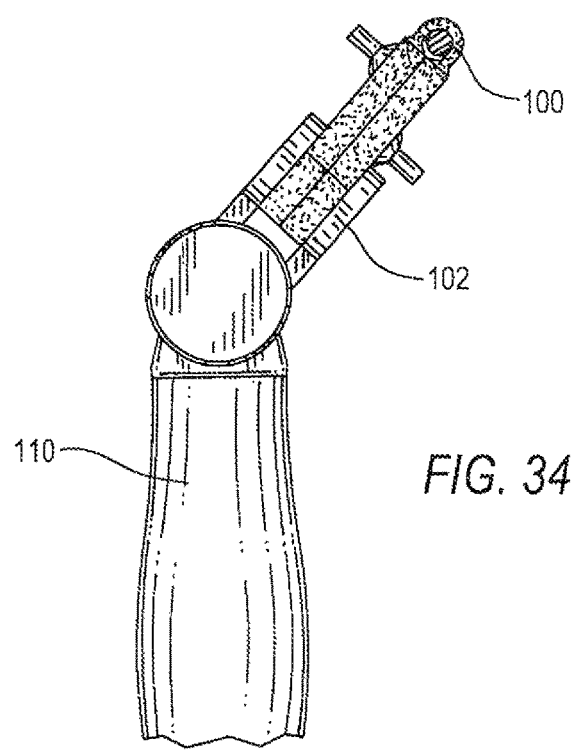
Figure 37:
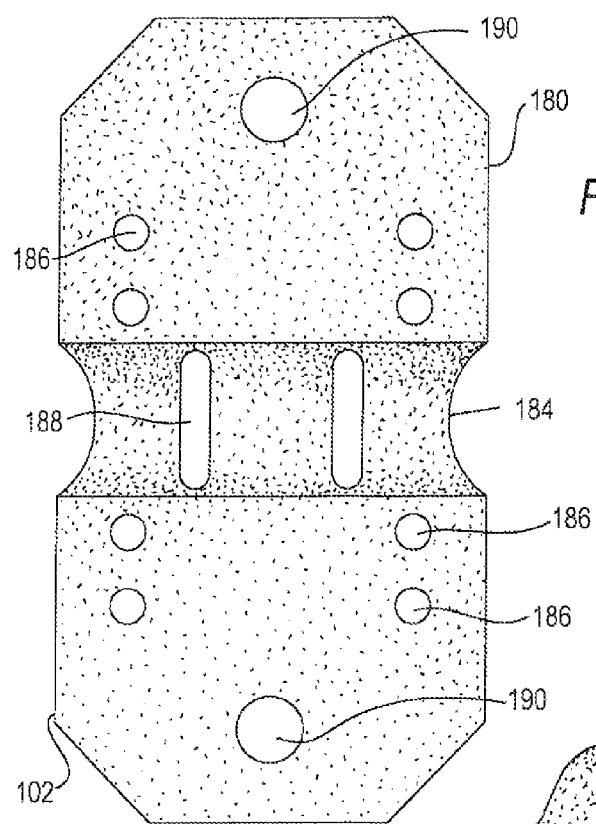
FIG. 37 shows a plan view of the sleeve before it is folded and wrapped around the shaft of the surgical instrument.
Figure 38:
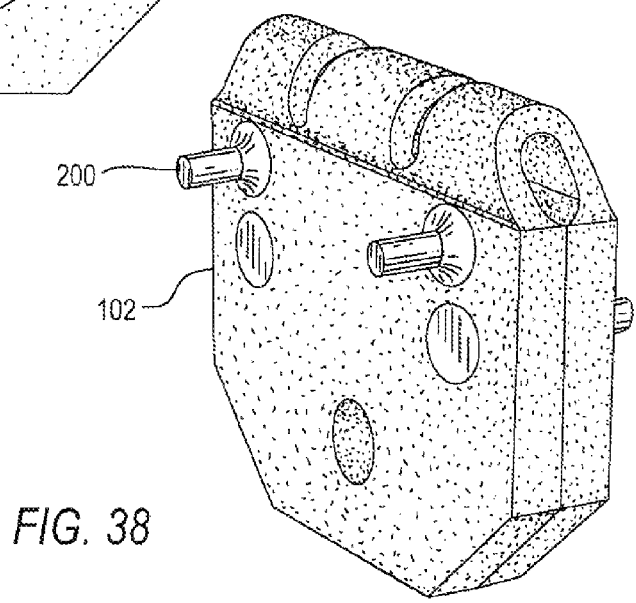
FIG. 38 shows an isometric view of the sleeve being folded with its leaves disposed in a juxtaposed position.

The leaves 182, 184 are then introduced between the wings 148, 150, The two wings at this stage are free rotate with respect to the axis of bosses 144, 146 and they are rotated toward the sleeve 102 until the bosses 162, 164 penetrate the central holes 190. At the same time the teeth or spikes 168, 170 penetrate the soft body of sleeve 102. In this manner, the sleeve 102 is firmly seated and held between the wings 148, 150. In order to make sure that the wings maintain their relative close position and keep their grasp on the sleeve 102, the screw 130 is tightened somewhat thereby making it somewhat difficult for the wings to be turned. Next, a person, such as the physician or other attendant preferably assisting the physician rotates the two wings and the sleeve to a desirable angular position for the shaft 102. This angle is selected to insure that the shaft 106 is in an optimal position for a particular surgery. Once this optimal position is reached, the screw 130 is tightened more thereby fixing the angular position of the wings with respect to the handle 110. If during surgery, the instrument with shaft 106 needs to be shifted or rotated with respect, the screw 130 can be turned to loosen the wings and reposition them angularly to a new surgical position. FIGS. 32, 33 and 34 show several configurations for the coupling attachment, with the sleeve 102 being at a different angle with respect to the grip 104.

At the end of the surgery, or if a new instrument is needed for an existing surgery, the screw 130 is untightened sufficiently to allow the sleeve 102 to be removed. The sleeve 102 is then removed from shaft 106 and the sleeve can be reused or a new one can be mounted as described. The handle 110 and sleeve 102 can be sanitized or discarded as desired.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention.

What is claimed is:

1. A coupling for holding a surgical instrument in position during a surgical procedure, said surgical instrument including a shaft, said coupling comprising:
    a sleeve including two leaves connected by a hinging element, said hinging element being arranged and constructed to wrap around the shaft and hold the shaft securely with said two leaves being disposed in an overlapping configuration, wherein each of said two leaves includes an inner leaf surface and wherein in said overlapping configuration said inner surfaces are in contact with each other; and
    a grip having a grip body configured and sized to be held by a person during die surgical procedure and a mounting element attached to said grip body and arranged and constructed to selectively engage and secure immovably said leaves;
    wherein said mounting element includes a first win and a second wing configured to move between a first wing position in which the wings are separated and a second wing position in which said wings cooperate to engage and secure said two leaves between said wings.

2. The coupling of claim 1 wherein said grip body defines a grip longitudinal axis and said wings are arranged and constructed to selectively pivot about a horizontal axis perpendicular to said grip longitudinal axis.

3. The coupling of claim 2 further comprising a tightening element mounted on said grip and arranged and constructed to tighten said wings in a predetermined position.

4. The coupling of claim 2 wherein said wings include a sleeve engaging member arranged and constructed to fixedly engage said sleeve.

5. A coupling for holding a surgical instrument in position during a surgical procedure, said surgical instrument including a shaft, said coupling comprising:
    a sleeve including two leaves connected by a hinging element, said hinging element being arranged and constructed to wrap around the shaft and hold the shaft securely with said two leaves being disposed in an overlapping configuration, wherein each of said two leaves includes an inner leaf surface and wherein in said overlapping configuration said inner surfaces are in contact with each other; and
    a grip having a grip body configured and sized to be held by a person during the surgical procedure and a mounting element attached to said grip body and arranged and constructed to selectively engage and secure said leaves, said mounting element including a first wing and a second wing configured to move between a first wing position in which the wings are separated and a second wing position in which said wings cooperate to engage and secure said two leaves between said wings; wherein said mounting element further includes a head formed integrally with said grip body and a holding element securing said wings to said head.

6. The coupling of claim 5 wherein said holding element is configured to hold said wings at a preselected angle with respect to said grip body.

7. The coupling of claim 5 wherein said grip body defines a body axis and said head defines a head axis disposed perpendicularly to said body axis, and wherein said wings are pivotable around said head axis.

8. The coupling of claim 7 wherein said holding element includes a locking element locking said wings at a predetermined angle with respect to said body axis.

9. The coupling of claim 8 wherein said holding element includes head bosses mounted on said head and said wings include wing bosses disposed between said head bosses, said holding element including a screw passing through said bosses and along said head axis.

10. The coupling of claim 5 wherein each wing has a leaf securing element securing the respective leaf to the wing.

11. The coupling of claim 5 wherein each leaf has an outer surface and wherein each wing is configured to engage the outer surface of a respective leaf.

12. The coupling of claim 11 wherein each wing includes a wing inner surface with a leaf engaging member and each leaf has a respective wing engaging member selectively engaging the respective leaf.

\* \* \* \* \*